United States Patent [19]

Griffin et al.

[11] Patent Number: 5,288,612

[45] Date of Patent: Feb. 22, 1994

[54] ASSAY METHODS FOR DETECTING SERUM PROTEASES, PARTICULARLY ACTIVATED PROTEIN C

[75] Inventors: John H. Griffin, Del Mar; Andras Gruber, San Diego, both of Calif.

[73] Assignee: The Scripps Research Institute, La Jolla, Calif.

[21] Appl. No.: 725,359

[22] Filed: Jul. 3, 1991

[51] Int. Cl.⁵ .............................................. C12Q 1/37
[52] U.S. Cl. ...................................... 435/23; 435/7.1; 436/548; 436/518
[58] Field of Search ............... 435/7.1, 23; 436/548, 436/518

[56] References Cited

PUBLICATIONS

Geiger et al., *Thrombosis and Haemostasis*, 61(1), pp. 86–92, 1989.
Heeb et al., *Blood*, 73, pp. 446–454; 455–461, 1989.
Comp, et al., *Blood*, 63: 15–21 (1984).
Exner, et al., *J. Lab. Clin. Med.*, 107: 405–411 (1986).
Gruber, et al., *Blood*, 73: 639–642 (1989).
Tabernero, et al., *Thromb. Haemost.*, 63: 380–382 (1990).

*Primary Examiner*—Ronald W. Griffin
*Assistant Examiner*—Pamela S. Webber
*Attorney, Agent, or Firm*—Douglas A. Bingham; Thomas Fitting; April C. Logan

[57] ABSTRACT

The invention describes diagnostic methods and compositions for determining the amount of protease in a body fluid sample. In particular, the invention detects proteases by a method in which both a reversible inhibitor of the protease and an irreversible inhibitor of interfering proteases during the detection step are employed to increase the sensitivity of the enzyme capture assay. The assay detects normal serum levels of activated protein C.

9 Claims, 3 Drawing Sheets

ASSAY METHODS FOR DETECTING SERUM PROTEASES, PARTICULARLY ACTIVATED PROTEIN C

TECHNICAL FIELD

The present invention relates to diagnostic methods and compositions useful for determining the amount of an active protease present in a body fluid sample. In addition, the invention relates to methods for making such compositions.

BACKGROUND

Proteases are proteolytic enzymes that catalyze the cleavage of peptide bonds in other proteins. The effect of such cleavage on protein molecules is diverse. In some instances proteolytic cleavage causes the cleaved protein to become inactive. In other instances proteolytic cleavage causes a once inactive protein to become activate. In yet other instances proteolytic cleavage is a mechanism whereby a single polypeptide precursor is cleaved into two or more individual polypeptides.

Proteolytic enzymes are grouped into families based on similar functions, active sites, amino acid sequences, and/or three-dimensional structures. Doolittle, *Science*, 214:149 (1981); and de Haen et al., *J. Mol. Biol.*, 92:225 (1975). Examples of protease families are the cytochrome c family, the globins, mammalian serine proteases, and the cyclic nucleotide-dependent protein kinase family. Within proteolytic enzyme families are distinct subfamilies which usually share a similar type of physiological activity.

For instance, the common denominator of members in the serine protease family is a shared functional domain, i.e., the catalytic domain defined by amino acid residues $Asp^{102}$, $Ser^{195}$, and $His^{57}$ of chymotrypsin. In addition, serine proteases sharing common physiological functions are categorized into subgroups. Examples of such subgroups are those containing serine proteases which function in the digestion, reproduction, and blood coagulation pathways.

Because proteases are involved in so many physiological processes, it is clinically useful to measure the level of a specific protease in body fluid samples. The measurement would indicate whether the specific protease is present at a level above or below that usually found in a body fluid sample, or may indicate whether a specific protease is present at at in situ, and may therefore provide a diagnostic index. Additionally, the measurement would provide insight into the fate of a specific protease administered to a patient in a therapeutic mode, or monitor the fate of a specific protease targeted by a therapeutic mode. A useful assay for a specific proteolytic enzyme should have the additional feature of indicating whether the specific proteolytic enzyme detected is "active" or capable of becoming activated.

An example of a protease for which measurement in a body fluid sample would be useful is activated protein C (APC), which is a member of the serine protease family subgroup involved in the blood coagulation pathway. Protein C (PC) is a zymogen, that is, it is inactive until converted into APC through interaction with thrombin, another serine protease active in the blood coagulation pathway. PC and APC are structurally different only in a dodecapeptide which is present at the amino-terminal end of PC and absence in APC. The 12 amino acid peptide is removed by proteolytic cleavage. The role of APC is to inactivate coagulation cofactors Va and VIIIa. Therefore, APC regulates thrombosis through its anti-thrombotic activity. In contrast to activation of PC by thrombin, APC is inactivated by the protein C inhibitors α-1-anti-trypsin, plasminogen activator inhibitor-1, α-2-antiplasmin, α-2-macroglobulin, and possibly other nonspecific proteases.

The level of APC and/or PC in a body fluid sample has medical relevance. For instance, the incidence of hereditary PC and protein S deficiency among thrombophilic patients [Gladson et al., *Thromb. Haemost.*, 59:18-22 (1988)] is higher than in the normal population [Miletich et al., *N. Engl. J. Med.*, 317:991-996 (1987)] and many patients have been described with heterozygous PC deficiency and familial thrombophilia [Griffin et al., *J. Clin. Invest.*, 68:1370-1373 (1981); Horellou et al., *Br. Med. J.*, 289:1285-1287 (1984); Bovill et al., *Blood*, 73:712-717 (1989)]. Complete deficiency of PC activity, whether inherited [Branson et al., *Lancet*, 2:1165-1168 (1983); Seligsohn et al., *N. Engl. J. Med.*, 310:559-562 (1984)], experimental [Taylor et al., *J. Clin. Invest.*, 79:918-925 (1987); Snow et al., *Circulation*, 82:III-769 (1990)], or acquired [Gruber et al., *Thromb. Res.*, 42:579-581 (1986); Mitchell et al., *N. Engl. J. Med.*, 317:1638-1642 (1987)], represents a potentially fatal condition.

Thrombotic complications of PC deficiency can be controlled with PC or APC replacement therapy (Seligsohn et al., Taylor et al., and Snow et al., supra) or liver transplantation [Casella et al., *Lancet*, 1:435–437 (1988). The presence of measurable quantities of APC-inhibitor complexes in plasma samples from patients with intravascular coagulation indicates that APC is generated in vivo [Heeb et al., *Blood*, 73:455-461 (1989); Tabernero et al., *Thromb. Haemost.*, 63:380-382 (1990)]. However, methods to detect unbound (free) APC in body samples have not been described except for assays measuring APC at elevated levels during APC infusion therapy of baboons. Gruber et al., *Blood*, 73:639-642 (1989). Thus, it is presently unknown if unbound APC is normally present in the vascular fluid, and if so, whether it can be measured.

Although it would be useful to detect the level of a functionally active protease with accuracy and sensitivity, including APC, in a body fluid sample, there are several limitations to achieving this goal. First, enzyme-activator interactions subsequent to sample collection will increase the activity of the protease to be measured. For example, PC present in a blood sample is activated by trace amounts of thrombin, thus increasing the level of APC measured to a value above that originally present, if at all, in a blood sample. Second, enzyme-inhibitor interactions subsequent to sample collection will decrease the activity of the protease to be measured. For example, APC which may be present in a blood sample is inactivated by any of a number of protease inhibitors, including those noted above, thus decreasing the level of APC to a value below that originally present, if at all, in a blood sample. Third, specificity of an assay depends on selective detection of the activity of only the protease desired to be detected. Thus, it is necessary to define a substrate that is highly specific for the protease to be detected. And, fourth, because proteases are present in the blood at very low concentrations, an assay to detect activity of a protease must be highly sensitive, without background interference due to factors such as those previously described.

Assays designed to detect APC in the blood have not overcome the obstacles delineated above and thus are not sufficiently sensitive to detect the activity of APC which might be present in a blood sample. For instance, Gruber et al., *Blood*, 73:639-642 (1989), describes an APC activity assay that measures the level of APC in the blood of baboons infused with APC. There, blood is drawn into benzamidine and citrate to block the serine protease activity in the blood sample and to inhibit complex formation between APC and its inhibitors. The treated blood then is contacted with the anti-PC monoclonal antibody C3 immobilized on microtiter plates, and the complex is washed to remove unbound blood constituents and benzamidine, a reversible inhibitor of APC. The washed complex is then contacted with a synthetic chromogenic substrate for APC and the amidolytic activity of APC is measured. The assay described in Gruber et al. supra was sensitive in the range of 0.005 to 5.0 ug/ml, a range suitable to detect the level of infused APC but too low to detect levels of APC which might be present in blood not infused with APC.

Another assay for APC activity described by Gruber et al., supra, is an APTT assay, i.e., an assay that measures the activated partial thromboplastin time (APTT) of plasma contacted with APC. Again, the data indicate that the APTT assay is useful in determining the level of APC in blood from a subject infused with APC, but is not sensitive enough to determine if APC is present in blood from a subject not infused with APC.

A functional assay for PC is described by Comp et al., *Blood*, 63:15-21 (1984). There, PC is activated in recalcified plasma by the thrombin-thrombomodulin complex, and contacted with immobilized anti-PC polyclonal antibodies. The activity of immobilized APC toward a synthetic substrate is measured. This assay provides an indication of the level of functional PC present in blood, i.e., PC that is capable of activation. The assay is not useful to determine the level of already activated PC, i.e., APC, that may be present in the blood.

The use of polyclonal antisera to measure PC activity also was described by Exner et al., *J. Lab. Clin. Med.*, 107:405-411 (1986). PC was captured on immobilized antisera, activated, and then reacted with a chromogenic substrate. The assay does not detect the level of APC actually present in a blood sample.

Thus, while functional assays to detect PC in the blood and to detect APC in blood infused with APC are known, there remains a need for sensitive assays to accurately detect whether an active protease such as APC is present in a body fluid sample and, if present, to quantitate its presence.

BRIEF SUMMARY OF THE INVENTION

It has now been discovered that a specific protease present in a body sample can be detected by methods which employ a reversible inhibitor of the specific protease to be detected and an irreversible inhibitor of interfering serine proteases present during the detection reaction that are not to be detected. A preferred aspect of this invention contemplates a method of detecting trace levels of the serine protease activated protein C in a body fluid sample.

Thus the present invention contemplates a method for determining the amount of a protease in a body fluid sample comprising the steps of:

a) contacting an immobilized antibody molecule composition, comprising antibody molecules affixed to a solid support, with an irreversible protease inhibitor in an amount of inhibitor sufficient to inhibit protease activity associated with the composition to form a first admixture, said antibody molecules having the capacity to immunoreact with a protease to form an immunoreaction complex having protease activity and the ability to bind a reversible inhibitor;

b) maintaining the first admixture for a time period sufficient for said irreversible inhibitor to inhibit the protease activity of the immobilized antibody molecule composition, and form a protease activity-free immobilized antibody composition;

c) removing excess irreversible inhibitor from the protease activity-free immobilized antibody composition formed in step (b);

d) admixing a body fluid sample with a coagulation inhibiting buffer containing a protease inhibiting amount of a reversible protease inhibitor, to form a second admixture;

e) admixing said second admixture with the protease activity-free antibody composition formed in step (c) to form an immunoreaction admixture having a liquid phase and a solid phase;

f) maintaining said immunoreaction admixture under immunoreaction conditions for a time period sufficient for protease present in said body sample to immunoreact with the antibody molecules present on the solid support and form a first solid-phase immunoreaction product;

g) removing the reversible inhibitor from said first solid phase immunoreaction product to form an inhibitor-free solid-phase immunoreaction product; and h) determining the amount of protease activity present in the inhibitor-free solid-phase immunoreaction product formed in step (g) and thereby the amount of protease in the body sample.

Also contemplated is a method for producing a protease activity-free immobilized antibody composition comprising:

a) contacting an immobilized antibody molecule composition, comprising antibody molecules affixed to a solid support, with an irreversible protease inhibitor in an amount of inhibitor sufficient to inhibit protease activity associated with the composition to form an inhibition admixture, said antibody molecules having the capacity to immunoreact with a protease to form an immunoreaction complex having protease activity and the ability to bind a reversible inhibitor;

b) maintaining the inhibition admixture for a time period sufficient for said irreversible inhibitor to inhibit the protease activity of the immobilized antibody molecule composition, and form a protease activity-free immobilized antibody composition; and c) removing the excess irreversible inhibitor from the protease activity-free immobilized antibody composition formed in step (b).

In addition, a protease activity-free immobilized antibody molecule composition is contemplated comprising anti-protease antibody molecules affixed to a solid support, said antibody molecules having the capacity to immunoreact with a protease to form an immunoreaction complex having protease activity and the ability to bind a reversible inhibitor, and said composition having a background level of protease activity when said composition is measured in an assay for said protease in the absence of a test protease.

BRIEF DESCRIPTION OF THE DRAWINGS

In the drawings forming a portion of this disclosure:

FIG. 1B shows the effect of preincubating the APC standards with polyclonal anti-PC antisera prior to detection in the ECA prior to the substrate incubation time of 3 days. Open circles represent untreated APC; triangles represent APC pretreated with anti-PC antisera. The data indicate that specificity of the ECA for PC and APC.

FIG. 2A presents the APC activity measured after a 25 day incubation in two different series of dilutions (represented by squares and circles) and in a serum sample assayed in an ECA plate not coated with anti-PC antibody. The data shown in FIG. 2B were generated when pooled serum samples (squares) were assayed for PCA activity by a 12 day incubation of substrate on the same plate as PCA standard (circles). In both panels, the triangle represents the APC activity measured in a sample contacted with an ECA assay plate that did not contain anti-PC antibody.

DETAILED DESCRIPTION OF THE INVENTION

A. Definitions

Figure 1A:
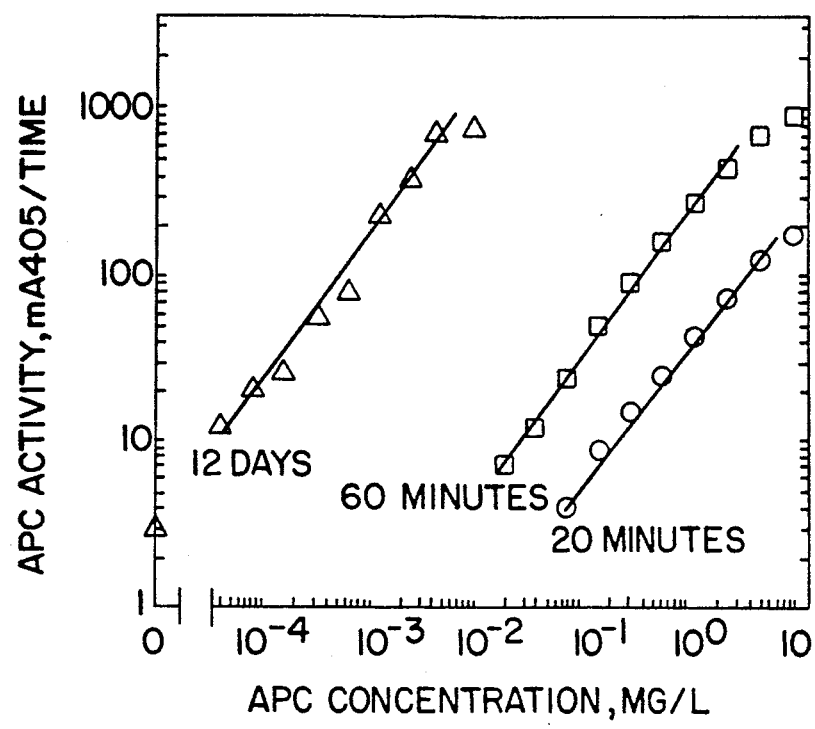
FIGS. 1A and 1B depict the APC activity measured in an enzyme capture assay (ECA) whereby a series of APC 4standards are captured by an immobilized anti-PC monoclonal antibody and then reacted with a chromogenic substrate specific for APC, as described in Example 5a. The standard curves shown in FIG. 1A represent the amidolytic activity measured after the immobilized antibody-APC complexes were incubated with substrate for 20 min, 60 min, or 12 days. The sensitivity of the ECA assay increased with increased incubation time.

Substrate: The term "substrate" as used herein refers to a small peptide which is catalytically acted upon by a specific proteolytic enzyme to form a substrate reaction product.

Functional Association: The term "functional association" as used herein refers to an association between two or more compositions in such a manner which allows the associated compositions to engage in the function usually attributed to their association. An example of functional association is the association of a protease and its substrate in such a way which allows the protease to react with its substrate in its usual manner.

Enzyme: The term "enzyme" as used herein refers to a protein or polypeptide capable of accelerating or producing by catalytic action some change in a substrate for which it is often specific.

B. Proteases and Protease Inhibitors

Proteases and protease inhibitors are employed in the methods and compositions of the present invention.

1. Proteases and Serine Proteases

The term "protease" as used herein refers to a protein that catalyzes the cleavage of peptide bonds in other proteins. Examples of proteases include renin, pepsin, collagenase, endopeptidase 24.11, enkephalinase, elastase, angiotensin converting enzyme, aminopeptidase, carboxypeptidases, and the like.

Proteases are typically characterized by particular amino acid residues located at the catalytic site of the enzyme. For example, in addition to the serine protease, such at trypsin, chymotrypsin and APC described as exemplary herein, there are also cysteine proteases, including papain and cathepsin, and the aspartic acid proteases, including HIV protease and "pepsin-like" proteases.

In preferred embodiments of the present methods and compositions the protease is a serine protease. The term "serine protease" as used herein refers to a member of a family of proteases that share a functional domain defined by amino acid residues $Asp^{102}$, $Ser^{195}$, and $His^{57}$ of chymotrypsin. Examples of serine proteases include those in the complement convertase family (e.g., factors Clr, Cls, D, C3 convertase); those in the plasminogen activator family (e.g., tissue plasminogen activator, urinary plasminogen activator); those in the blood coagulation pathway family (e.g., factors XIIIa, XIIa, XIa, Xa, IXa, VIIa, thrombin, plasma kallikrein, activated PC), those in the digestive enzyme family (e.g., trypsin, chymotrypsin, pancreatic elastase, enterokinase), those in the hormone family (e.g., tissue kallikrein, post proline cleaving enzyme), and the like.

Particularly preferred embodiments of the present methods and compositions are ones in which the protease is a serine protease active in the blood coagulation pathway. Especially preferred in this regard is APC.

2. Inhibitors

The term "inhibitor" is used herein to refer to a composition that associates with a protease in such a manner as to inhibit the normal function of the protease. Such inhibition can be effected by a variety of ways, including binding of the inhibitor to a site on the protease such that the substrate binding site is blocked through steric hinderance; binding of the inhibitor composition to the active site of the protease and thus preventing access of substrate to the active site, thus preventing its activity; binding of the inhibitor to the protease in such a manner that changes the secondary or tertiary structure of the protease and therefore inhibits its activity (allosteric effects); and other ways.

a. Reversible Inhibitors

The term "reversible inhibitor" is used herein to refer to a protease inhibitor that associates with a protease in such a way as to inhibit the activity of the protease while the protease and inhibitor are bound, but does not associate with a protease in such a way as to inhibit the activity of the protease when the protease and inhibitor are no longer bound. Reversible inhibitors can effect inhibition by competing with substrate for binding to the active site of the protease (competitive reversible inhibitor), or by associating with the protease bound to its substrate in a way to make the complex inactive (uncompetitive reversible inhibitor), or by associating with the protease and/or protease-substrate complex in a way that inhibits the activity of either and/or both.

Reversible inhibitors have been defined for a variety of proteases. For example, reversible aspartic protease inhibitors include substrate derived peptides (e.g., RIP), activation sequence peptides, and pepstatin-derived and statin containing inhibitors (SCRIP); examples of reversible cysteine protease inhibitors are substrate-derived peptides and peptide aldehydes (e.g., antipain, leupeptin); reversible metalloprotease inhibitors include EDTA, peptide inhibitors, peptide bond replacements (e.g., ketones), phosphoramidon and phosphorus containing inhibitors, hydroxamic acid derivatives of peptides, thiol derivatives of peptides (e.g., captopril), and carboxyl-containing and bi-product analogue inhibitors (e.g., succinic acid).

Particularly preferred reversible inhibitors useful in the present invention are those specific for serine proteases. Such reversible inhibitors include those in the peptide aldehyde and ketone class (e.g., chymostatin, leupeptin, antipain, 4-amidinophenylpyruvic acid), those in the boric acid class (e.g., ethylboronic acid, R-Boro-Ala), peptide inhibitors (e.g., aprotinin and soya bean trypsin inhibitor derivatives, and alpha-1-PI derivatives), benzamidines, and lysine and arginine derivatives (e.g., epsilon-aminocaproic acid, $N^{\alpha}$(arylsulphonyl)arginine amides).

Especially preferred reversible inhibitors are those specific for serine proteases active in the blood coagulation pathway, with those specific for APC being most preferred. Examples of reversible inhibitors specific for APC include benzamidine and aprotinin.

b. Irreversible Inhibitors

The term "irreversible inhibitor" as used herein refers to a protease inhibitor that associates with a protease in such a way as to permanently inhibit the activity of the protease. Such inhibition is typically by permanent covalent modification of a functional group on the protease required for catalysis.

The irreversible inhibitors employed in the present methods and compositions are specific for serine proteases. Examples of irreversible serine protease inhibitors include phenylmethanesulfonyl fluoride (PMSF; available from Sigma Chem. o., St. Louis, Mo.), (p-amidinophenyl)methanesulfonyl fluoride (pAPMSF; available from Chemicon, El Segundo, Calif.), and diisopropylfluorophosphate (DFP; available from Sigma Chem Co., St. Louis, Mo.).

C. Antibodies and Antibody Compositions

Antibody and antibody compositions are employed in the methods and compositions of the present invention.

The term "antibody" in its various grammatical forms is used herein to refer to immunoglobulin molecules and immunologically active portions of immunoglobulin molecules, i.e., molecules that contain an antibody combining site or paratope. Illustrative antibody molecules are intact immunoglobulin molecules, substantially intact immunoglobulin molecules and those portions of an immunoglobulin molecule that contain the paratope, including those portions known in the art as Fab, Fab', F(ab')2 and F(v).

Fab and F(ab')2 portions of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')2 portions followed by reduction of the disulfide bonds linking the two heavy reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

The term "antibody combining site" refers to that structural portion of an antibody molecule comprised of a heavy and light chain variable and hypervariable regions that specifically binds (immunoreacts with) antigen. The term "immunoreact" in its various forms is used herein to refer to binding between an antigenic determinant-containing molecule and a molecule containing an antibody combining site such as a whole antibody molecule or a portion thereof.

As used herein, the term "specifically bound" refers to a non-random binding reaction between an antibody molecule and an antigenic determinant-containing molecule, or a receptor and a ligand molecule. Illustrative of a specifically-bound antibody-antigen complex is that between antibody C3-Mab (see Example 1) and APC or PC.

The term "antigenic determinant" refers to the actual structural portion of the antigen that is immunologically bound by an antibody combining site. The term is also used interchangeably with "epitope".

An antibody used in the present invention, i.e., an anti-protease antibody, is characterized as comprising antibody molecules that are capable of immunoreacting with a preselected protease.

In addition, an anti-protease antibody for use in this invention is characterized as comprising antibody molecules capable of immunoreacting with a preselected protease when complexed with a reversible inhibitor, i.e., a protease-reversible inhibitor complex to form a protease-inhibitor immunoreaction product. The anti-protease antibody must also immunoreact with a site on the protease-reversible inhibitor complex that does not prevent subsequent functional association of the protease with its substrate when the reversible inhibitor has been removed from the protease. Thus the antibody molecules have he capacity to immunoreact with a protease to form an immunoreaction complex having protease activity and the ability to bind a reversible inhibitor. Stated differently, an anti-protease antibody useful in the present methods immunoreacts with a protease that is complexed with a reversible inhibitor in the form of a protease-reversible inhibitor complex such that the antibody does not inhibit proteolytic cleavage of its substrate.

In preferred embodiments, the antibody immunoreacts with APC and the reversible protease inhibitor in the protease-inhibitor immunoreaction complex is benzamidine.

Antibody immunoreactivity with a preselected protease-containing antigen can be measured by a variety of immunological assays known in the art. Exemplary immunoreaction of an anti-protease antibody with APC is described in Example 1 and elsewhere. Immunoreaction of an immobilized anti-protease antibody with a preselected protease when complexed with a reversible inhibitor can be assayed at least by the methods described in Example 5.

1. Polyclonal Antibodies

An antibody of the present invention is typically produced by immunizing a mammal with an inoculum containing a preselected protease, or a preselected protease complexed with a reversible inhibitor to form a protease-reversible inhibitor complex as the immunogen and thereby induce in the mammal a population of antibody molecules having immunospecificity for a preselected protease or the protease-reversible inhibitor complex. Such mammal-produced populations of antibody molecules are referred to as "polyclonal" because the population comprises antibodies with differing immunospecificities and affinities for the immunogen. The antibody molecules are then collected from the mammal and isolated to the extent desired by well known techniques such as, for example, by using DEAE Sephadex to obtain the IgG fraction.

To enhance the specificity of the antibody, the antibodies may be purified by immunoaffinity chromatography using solid phase-affixed immunogen. The antibody is contacted with the solid phase-affixed immunogen for a period of time sufficient for the immunogen to immunoreact with the antibody molecules to form a solid phase-affixed immunocomplex. The bound antibodies are separated from the complex by standard techniques.

The antibody so produced can be used, inter alia, in the diagnostic methods and compositions of the present invention to detect a preselected protease present in a body sample. See, for example, the method described in Example 5.

The word "inoculum" in its various grammatical forms is used herein to describe a composition containing a preselected protease or protease-reversible inhibitor complex as an active ingredient used for the preparation of antibodies against a preselected protease or protease-reversible inhibitor complex.

A convenient means to produce an antibody useful for the methods and compositions herein is to utilize a polypeptide whose amino acid sequence is derived from the protease to which the antibody is to immunoreact. Preferred polypeptides are located at surface regions of the protease away from the region of the catalytic site so that the antibody does not inhibit catalysis of substrate.

The inoculum contains an effective, immunogenic amount of a preselected protease, protease-reversible inhibitor complex, or polypeptide based on the protease as described before. When the inoculum contains a polypeptide, it typically is a conjugate linked to a carrier. The effective amount of protease, complex or polypeptide per unit dose sufficient to induce an immune response to the immunogen depends, among other things, on the species of animal inoculated, the body weight of the animal and the chosen inoculation regimen as is well known in the art. Inocula typically contain protein or polypeptide concentrations of about 10 micrograms to about 500 milligrams per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the protease-protease-reversible inhibitor-, or polypeptide-conjugate by dispersing the conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

When a polypeptide is used in an inoculum to induce antibodies it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides of this invention are collectively referred to herein by the term "polypeptide", and its various grammatical forms.

For a polypeptide that contains fewer than about 35 amino acid residues, it is preferable to use the peptide bound to a carrier for the purpose of inducing the production of antibodies.

One or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, dialdehydes such as lutaraldehyde, Klipstein, et al., *J. Infect. Dis.*, 147:318-326 (1983) and the like, or the use of carbodiimide technology as in the use of a water-soluble carbodiimide to form amide links to the carrier. for a review of protein conjugation or coupling through activated functional groups, see Aurameas, et al., *Scand. J. Immunol.*, 1:7-23 (1978).

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The techniques of polypeptide conjugation or coupling through activated functional groups presently known in the art are particularly applicable. See, for example, Aurameas, et al., *Scand. J. Immunol.*, Vol. 8, Suppl. 7:7-23 (1978); and U.S. Pat. No. 4,493,795, No. 3,791,932 and No. 3,839,153. In addition, a site directed coupling reaction can be carried out so that any loss of activity due to polypeptide orientation after coupling can be minimized. See, for example, Rodwell et al., *Biotech.*, 3:889-894 (1985), and U.S. Pat. No. 4,671,958.

One or more additional amino acid residues may be added to the amino- or carboxy-termini of the polypeptide to assist in binding the polypeptide to form a conjugate. Cysteine residues, usually added at the carboxy-terminus of the polypeptide, have been found to be particularly useful for forming conjugates via disulfide bonds, but other methods well-known in the art for preparing conjugates may be used.

A preferred anti-protease antibody for use in the present methods and compositions is a monoclonal antibody and is used herein as exemplary of the invention in its various embodiments.

2. Monoclonal Antibodies

The phrase "monoclonal antibody composition" in its various grammatical forms refers to a population of antibody molecules that contain only one species of antibody combining site capable of immunoreacting with a particular antigen. A monoclonal antibody composition thus typically displays a single binding affinity for any antigen with which it immunoreacts. A monoclonal antibody composition may therefore contain an antibody molecule having a plurality of antibody combining sites, each immunospecific for a different antigen, e.g., a bispecific monoclonal antibody.

A monoclonal antibody of this invention comprises antibody molecules as described herein, namely that immunoreact with a protease that is complexed with a reversible inhibitor in the form of a protease-reversible inhibitor complex such that they do not inhibit proteolytic cleavage of the substrate for the protease.

A monoclonal antibody composition is typically composed of antibodies produced by clones of a single cell called a hybridoma that secretes (produces) but one kind of antibody molecule. The hybridoma cell is formed by fusing an antibody-producing cell and a myeloma or other self-perpetuating cell line. Such antibodies were first described by Kohler and Milstein, *Nature* 256:495–497 (1975), which description is incorporated herein by reference. The hybridoma supernates so prepared are then screened for the presence of antibody molecules having the immunoreactive properties as described further herein.

The monoclonal antibody compositions of the present invention may be produced by the following method, which comprises the steps of:

(a) Immunizing an animal with a protease. Preferably, the immunogen is a serine protease. It is most preferred that the serine protease be a member of the blood coagulation family; APC or PC or a mixture of both is especially preferred in this regard. In a preferred embodiment the immunogen comprises protease bound to a reversible inhibitor.

The immunization is typically accomplished by administering the immunogen to an immunologically competent mammal in an immunologically effective amount, i.e., an amount sufficient to produce an immune response. Preferably, the mammal is a rodent such as a rabbit, rat or mouse. The mammal is then maintained for a time period sufficient for the mammal to produce cells secreting antibody molecules that immunoreact with the protease immunogen. Such immunoreaction is detected by screening the antibody molecules so produced for immunoreactivity with a preparation of the immunogen protein. Optionally, it may be desired to screen the antibody molecules with a preparation of the protein in the form in which it is to be detected by the antibody molecules in an assay, e.g., a protease associated with a reversible inhibitor. These screening methods are well known to those of skill in the art, and are described in Example 1 with regard to anti-PC antibodies.

(b) A suspension of antibody-producing cells removed from each immunized mammal secreting the desired antibody is then prepared. This is typically accomplished by removing the spleen of the mammal and mechanically separating the individual spleen cells in a physiologically tolerable medium using methods well known in the art.

(c) The suspended antibody-producing cells are treated with a transforming agent capable of producing a transformed ("immortalized") cell line. Transforming agents and their use to produce immortalized cell lines are well known in the art and include DNA viruses such as Epstein Bar Virus (EBV), Simian Virus 40 (SV40), Polyoma Virus and the like, RNA viruses such as Moloney Murine Leukemia Virus (Mo-MuLV), Rous Sarcoma Virus and the like, myeloma cells such as P3X63-Ag8.653, Sp2/0-Ag14 and the like.

It is preferred that the myeloma cell line used to prepare a hybridoma be from the same species as the lymphocytes. Typically, a mouse of the strain 129 G1X+ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

In preferred embodiments, treatment with the transforming agent results in the production of a hybridoma by means of fusing the suspended spleen cells with mouse myeloma cells from a suitable cell line by the use of a suitable fusion promoter. The preferred ratio is about 5 spleen cells per myeloma cell in a suspension containing about $10^8$ splenocytes. A preferred fusion promoter is polyethylene glycol having an average molecule weight from about 1000 to about 4000 (commercially available as PEG 1000, etc.); however, other fusion promoters known in the art may be employed.

The cell line used should preferably be of the so-called "drug resistant" type, so that unfused myeloma cells will not survive in a selective medium, while hybrids will survive. The most common class is 8-azaguanine resistant cell lines, which lack the enzyme hypoxanthine-guanine phosphoribosyl transferase and hence will not be supported by HAT (hypoxanthine, aminopterin, and thymidine) medium. It is also generally preferred that the myeloma cell line used be of the so-called "non-secreting" type which does not itself produce any antibody. In certain cases, however, secreting myeloma lines may be preferred.

(d) The transformed cells are then cloned, preferably to monoclonality. The cloning is preferably performed in a tissue culture medium that will not sustain (support) non-transformed cells. When the transformed cells are hybridomas, this is typically performed by diluting and culturing in separate containers the mixture of unfused spleen cells, unfused myeloma cells, and fused cells (hybridomas) in a selective medium which will not sustain the unfused myeloma cells. The cells are cultured in this medium for a time sufficient to allow death of the unfused cells (about one week). The dilution can be a limiting dilution, in which the volume of diluent is statistically calculated to isolate a certain number of cells (e.g., 1–4) in each separate container (e.g., each well of a microtiter plate). The medium is one (e.g., HAT medium) that will not sustain the drug-resistant (e.g., 8-azaguanine resistant) unfused myeloma cell line.

(e) The tissue culture medium of the cloned transformants is analyzed (or assayed) to detect the presence of secreted anti-protease antibody molecules using well known immunological techniques. Preferably the medium is monitored for the presence of anti-serine protease antibody molecules, and more preferably anti-blood coagulation pathway serine protease antibody molecules, with anti-APC antibody molecules are especially preferred in this regard. As noted in step (a), methods for such monitoring are known to those of skill in the art; the specifics of each method will depend on the desired specificity of the antibody molecules as described herein and the initial immunogen.

(f) A desired transformant is then selected and grown in an appropriate tissue culture medium for a suitable length of time, followed by recovery (harvesting) of the desired antibody from the culture supernatant by well known techniques. The suitable medium and suitable length of culturing time are also well known or are readily determined.

A particularly preferred monoclonal antibody is the monoclonal antibody produced by the hybridoma 22A101C53B2 (Mab C3) that immunoreacts with APC and PC, and With APC bound to benzamidine as described herein. MAb C3 was produced as described in Example 1 using purified PC as the immunogen.

Hybridoma C3 has been deposited pursuant to Budapest Treaty requirements with the American Type Culture Collection (ATCC), Rockville, Md., on Jul. 3, 1991, and was assigned accession number HB 10820.

Hybridoma C3 was deposited in a depository affording permanence of the deposit and ready accessibility thereto by the public upon the issuance of a patent, under conditions which assure that access to the hybridoma will be available during the pending of the patent application to those deemed by the Commissioner to be entitled to such access, and that all restrictions on the availability to the public of the hybridoma as deposited will be irrevocably removed upon the granting of the patent. The deposited hybridoma will be maintained by the ATCC for the term of the patent or 30 years from the date of deposit, whichever is longer, and in all events for at least five years after the date of the last request for access.

To produce a much greater concentration of slightly less pure monoclonal antibody, the desired hybridoma can be transferred by injection into mice, preferably syngenic or semisyngenic mice, to generate ascites fluid. The hybridoma will cause formation of antibody-producing tumors after a suitable incubation time, which will result in a high concentration of the desired antibody (about 5–20 mg/ml) in the bloodstream and peritoneal exudate (ascites) of the host mouse.

Media and animals useful for the preparation of these compositions are both well known in the art and commercially available and include synthetic culture media, inbred mice and the like. An exemplary synthetic medium is Dulbecco's minimal essential medium (DMEM; Dulbecco et al., 1959, Virol. 8:396) supplemented with 4.5 gm/l glucose, 20 mM glutamine, and 20% fetal caf serum. An exemplary inbred mouse strain is the Balb/c.

Representative and preferred methods for producing anti-protease monoclonal antibody compositions are described in Example 1 for anti-APC monoclonal antibody.

A monoclonal antibody composition can also be produced by other methods well known to those skilled in the art of producing chimeric antibodies. Those methods include isolating, manipulating, and expressing the nucleic acid that codes for all or part of an immunoglobulin variable region including both the portion of the variable region comprised by the variable region of immunoglobulin light chain and the portion of the variable region comprised by the variable region of immunoglobulin heavy chain. Methods for isolating, manipulating, and expressing the variable region coding nucleic acid in procaryotic and eucaryotic hosts are disclosed in Robinson et al., PCT Publication No. WO 89/0099; Winter et al., European Patent Publication No. 0239400; Reading, U.S. Pat. No. 4,714,681; Cabilly et al., European Patent Publication No. 0125023; Sorge et al., *Mol. Cell Biol.*, 4:1730–1737 (1984); Beher et al., *Science*, 240:1041–1043 (1988); Skerra et al., *Science*, 240:1030–1041 (1988); and Orlandi et al., *Proc. Natl. Acad. Sci., U.S.A.*, 86: 3833–3837 (1989). Typically the nucleic acid codes for all or part of an immunoglobulin variable region that binds a preselected antigen (ligand). Sources of such nucleic acid are well known to one skilled in the art and, for example, may be obtained from a hybridoma producing a monoclonal antibody that binds the preselected antigen, or the preselected antigen may be used to screen an expression library coding for a plurality of immunoglobulin variable regions, thus isolating the nucleic acid.

3. Immobilization of Antibody Molecules

Antibodies useful in the present methods are immobilized onto (affixed to) a solid support to form an immobilized antibody composition. Antibodies can be affixed to a solid support by methods generally known in the art. A typical method of affixing to a solid support (matrix) is by adsorption from an aqueous medium, although other modes of affixation applicable to antibodies, well known to those skilled in the art, can be used. A preferred method of immobilization is described in Example 2.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

D. Protease Activity-free Immobilized Anti-Protease Antibody Compositions and Methods for Their Preparation The present invention contemplates a protease activity-free immobilized antibody molecule composition comprising anti-protease antibody molecules as described herein affixed to a solid support. As used herein, the phrase "protease-free" refers to a level of protease activity associated with the immobilized antibody composition that is sufficiently low that reaction of the composition with a protease substrate does not occur to a level that interferes with the assay in which the composition is to be utilized, i.e., a background level. Thus, the level of protease activity associated with a protease-free immobilized monoclonal antibody composition is a background level or below. Particularly preferred are serine protease activity-free immobilized antibody compositions.

The level of background protease activity, or changes in protease activity during inhibition procedures, can be evaluated by a variety of methods known to those of skill in the art. For instance, a convenient way of testing for proteases and confirming their removal is provided by use of commercially available Protease Substrate Gel tablets (Bio-Rad Laboratories, Richmond, Calif.). An alternative method to detect the level of protease activity is to contact an immobilized antibody composition with a substrate specific for the protease of interest and thereafter determine if the substrate was acted upon by a protease which may be present in the antibody composition. This latter method is described in Example 3b, wherein the hydrolysis of a chromogenic synthetic substrate by residual protease remaining in an immobilized antibody composition after treatment with the irreversible serine protease inhibitor paMPSF is compared to the hydrolysis of substrate by contaminating proteases present in the composition not so treated. An irreversible protease inhibitor-treated immobilized antibody composition exhibits a background level, where as an untreated composition can contain unacceptable levels of protease activity. As described in Example 3b, hydrolysis of the protease substrate was faster in immobilized antibody compositions not made protease-free, compared to those treated with an irreversible protease inhibitor. Thus, the treated antibody composition exhibited lower protease activity indicating that the inhibitor was effective in inhibiting proteases in the immobilized antibody composition.

When immobilized, the anti-protease antibody composition contains antibody molecules that are capable of immunoreacting and capturing the preselected protease present n a body fluid sample. The term "capture" refers to the effect of immunoreaction between the immobilized antibody molecule and its antigenic protease present in the body fluid sample to be analyzed, i.e., capture removes the protease from the fluid phase and immobilizes it in a solid phase complex.

The term "immobilized" refers to the affixed state of the antibody composition to a solid support.

Thus, in one embodiment, the invention contemplates a protease-free immobilized antibody molecule composition comprising antibody molecules affixed to a solid support, said composition having a background level of protease activity.

A "preselected protease" for immunoassay using an immobilized antibody composition can be any protease present in a body fluid sample for which antibody molecules specific therefor can be made or are known.

The immobilized antibody composition is made protease-free by methods which decrease the measurable level of protease activity associated with he antibody composition. Such methods include treating (contacting) the composition with a protease-inhibiting amount of an irreversible protease inhibitor for a time period sufficient to reduce and therefor inhibit the protease activity associated with immobilized antibody composition.

Thus, in another embodiment, the invention contemplates a protease activity-free immobilized antibody molecule composition comprising antibody molecules affixed to a solid support produced by treating the composition with a protease-inhibiting amount of an irreversible protease inhibitor for a time period sufficient measurably reduce (inhibit) the protease activity of the composition.

The sensitivity of the enzyme capture assay is increased through the inhibition of background-producing serine proteases that are present on the immobilized antibody composition and that activate substrate conversion. The additional effect of inhibiting the background-producing serine proteases is the maintenance and preservation of specifically desired serine proteases as well as the immobilized antibody composition.

An assay is described here to screen for preferred inhibitors which would irreversibly inhibit the substrate-converting activity of the undesirable background-producing serine proteases, thereby resulting in a lowering or a decrease of detectable background in normal assay conditions. For selecting appropriate inhibitors of the background-producing serine proteases, separate wells of a microtiter plate are provided having an antibody directed against a desired serine protease in the form of antibody-coated wells as an immobilized antibody composition. A preferred antibody of this invention is the anti-PC monoclonal antibody described in Example 1.

Various serine protease inhibitors ranging in concentration from 0 to 500 uM are then separately admixed to the antibody-coated wells to form a solid:liquid phase antibody:inhibitor admixture. The admixtures are maintained for a time sufficient for the inhibitor to bind the background serine proteases. After binding, the unbound inhibitor is removed by washing the wells, the activity of the background-producing serine proteases present in the wells is measured by monitoring the change of absorbance of an added chromogenic substrate.

A serine protease inhibitor which irreversibly inhibits the background-producing serine protease is detected by the reduction or complete absence of a change in absorbance indicating little or no substrate conversion. The amount of background reduction produced by the serine protease inhibitor is calculated as the difference between the amount of substrate converted in the absence of inhibitor compared to that in the presence of inhibitor. The serine protease inhibitor which results in the greatest degree of irreversible inhibition of background-producing serine proteases is then selected as a preferred inhibitor for use in this invention. The selected inhibitor can then also be assayed for its ability to irreversibly inhibit background protease activity for an extended period of time, such as 12 hours.

Serine protease inhibitors contemplated for use in producing a serine protease-free antibody composition are of the irreversible type. Preferred inhibitors are phenylmethanesulfonyl fluoride (PMSF; available from Sigma Chem. Co., St. Louis, Mo.), (p-amidinophanyl)-methanesulfonyl fluoride (pAPMSF; available from Chemicon, El Segundo, Calif.), and diisopropylfluorophosphate (DFP; available from Sigma Chem. Co., St. Louis, Mo.). However any composition or manipulation that effects inhibition of serine protease activity is encompassed by this invention.

A "serine protease-inhibiting amount" of a serine protease inhibitor is that amount of inhibitor sufficient to effect inhibition of serine proteases associated with an immobilized antibody composition. Changes in the level of serine protease activity associated with an immobilized antibody composition can be followed by the assay for protease activity described herein. Measurable decreases in protease activity reflect effective inhibition for the purposes of this invention. Time periods sufficient to reduce the serine protease activity are time periods of contact between the immobilized antibody composition and the serine protease inhibitor that produce a measurable decrease in the detectable protease activity.

Typical time periods for irreversible inhibition of serine proteases depends on the type of inhibitor, and the concentration used for inhibition, which conditions can be adjusted empirically by the skilled practitioner, but may range from seconds to hours, as may be desirable, so long as the measured inhibition is effected.

A representative method for producing a serine protease-free immobilized antibody composition by treating the composition with a serine protease-inhibiting amount of a serine protease inhibitor is described in Example 3a. In that example, the preferred amount of inhibitor and time period for inhibition was 250 $\mu$l pAMPSF or DFP/well for 30 min at 4° C.

The present invention therefor contemplates a method for making protease activity-free immobilized antibody compositions.

The method for producing a protease activity-free immobilized antibody composition comprises the steps of:

a) contacting an immobilized antibody molecule composition comprising antibody molecules affixed to a solid support with an irreversible protease inhibitor in an amount of inhibitor sufficient to inhibit protease activity associated with the composition, said contacting forming an inhibition admixture; and b) maintaining the inhibition admixture for a time period sufficient for said irreversible inhibitor to measurably reduce (inhibit) the protease activity of the immobilized antibody molecule composition; and c) removing the excess, unbound irreversible inhibitor from the protease activity-free immobilized antibody composition formed in step (b) to form a serine protease-free immobilized antibody composition.

Contacting in step (a) is by any method which allows the immobilized antibody composition to be acted upon by the irreversible protease inhibitor. One method of contacting is described in Example 3a, wherein an aqueous irreversible serine protease inhibitor is added to wells in a 96 well plastic dish to which antibodies are immobilized. The irreversible protease inhibitor in step (a) can be any inhibitor which reduces the level of protease associated with the immobilized antibody composition. Preferred irreversible inhibitors for serine proteases are PMSF, pAPMSF, and DFP.

The amount of inhibitor sufficient to inhibit a serine protease activity associated with the composition is any amount of inhibitor that will effect decreased serine protease activity when measured in the assays described in the Examples. A representative amount of inhibitor is described in Example 3a, wherein 250 $\mu$l of pAPMSF of DFP are employed.

The inhibition mixture is maintained in step (b) for a time period sufficient for the irreversible inhibitor to come in contact with serine proteases and inactivate them. A representative sufficient time period is described in Example 3a, wherein the irreversible inhibitor pAPMSF or DFP is contacted with the immobilized antibody preparation for 30 min.

Furthermore, the amount and time of incubation are defined by that amount and time which causes an immobilized antibody molecule composition to have a measurable change in the level of protease activity. Those of skill in the art will know how to prepare standards of the protease to be determined, and generate a standard curve using the protease-free immobilized antibody composition. The level of inhibition of the protease activity will be considered sufficient when a standard curve can be generated in the concentration range in which the concentration of a preselected protease to be measured is detected in normal patient's plasma. Methods for preparing a protease standard and generating a standard curve are described in Examples 4c and 6.

In step (c), unbound, excess irreversible inhibitor is removed from the protease-free immobilized antibody composition by any method effective to remove the irreversible inhibitor without interfering with or otherwise hindering the capacity of the immobilized antibody to immunoreact with its target antigen as described herein. Typically, removal involves exposing the irreversible inhibitor to one or more, preferably a series of, aqueous solutions (washes) having solutes designed to perturb the non-specific binding interaction between the protease inhibitor and the solid support such that rinsing effectively removes the inhibitor from the support. Thereafter, the solid support is recovered from the wash buffers to form an inhibitor-free immobilized antibody composition. Alternatively, the chemical instability of the inhibitor, such as low pH, can be utilized to inactivate the residual inhibitors present after treatment. One method of removal is to subject the immobilized antibody composition to a series of washes, as described in Example 3a.

Representative monoclonal antibody useful for producing a prefered composition that comprises a serine protease activity-free immobilized antibody molecules are those described in Example 1 for APC. Particularly preferred is a monoclonal antibody composition that is produced by the hybridoma C3-Mab. In another preferred embodiment, the antibody molecules immunoreact with a serine protease active in the blood coagulation pathway, with APC being especially preferred.

E. Diagnostic Methods

Also contemplated by the present invention are various methods for determining the amount of protease in a body fluid sample using protease activity-free immobilized anti-protease monoclonal antibody compositions to capture the protease to be detected. The activity of the protease comprising one member of the immunoreaction product thus formed is subsequently determined, which determination relates, either directly or indirectly, to the amount of protease in the sample.

In one embodiment, the present invention contemplates a method for determining the amount of a protease in a body fluid sample, said method comprising the steps of:

a) contacting an immobilized antibody molecule composition, comprising antibody molecules affixed to a solid support, with an irreversible protease inhibitor in an amount of inhibitor sufficient to inhibit protease activity associated with the composition, said antibody molecules having the capacity to immunoreact with a protease to form an immunoreaction product (complex), i.e., a protease that is complexed with a reversible inhibitor, said complex having protease activity and the ability to bind a reversible inhibitor, and said contacting forming a first admixture;

b) maintaining the first admixture for a time period sufficient for said irreversible inhibitor to measurably reduce (inhibit) the protease activity of the immobilized antibody molecule composition and form a protease activity-free immobilized antibody composition;

c) removing excess irreversible inhibitor from the protease activity-free immobilized antibody composition formed in step (b);

d) admixing a body fluid sample with a coagulation inhibiting buffer containing a protease inhibiting amount of a reversible protease inhibitor to form a second admixture;

e) admixing said second admixture with the protease activity-free antibody composition formed in step (c) to form an immunoreaction admixture having a liquid phase and a solid phase;

f) maintaining said immunoreaction admixture under immunoreaction conditions for a time period sufficient for protease present in said body sample to immunoreact with the antibody molecules present on the solid support and form a first solid-phase immunoreaction product;

g) removing the reversible inhibitor from said first solid phase immunoreaction product to form an inhibitor-free solid phase immunoreaction product; and h) determining the amount of protease activity present in the inhibitor-free solid-phase immunoreaction product formed in step (g) and thereby the amount of serine protease in the body sample.

As used herein, the phrase "body fluid sample" refers to an aliquot of a body fluid such as blood, plasma, serum, urine, saliva, and the like.

The method contemplates determination of a variety of proteases. A protease to be determined using the composition can be any protease present in a body fluid sample for which antibody molecules specific therefor can be made or are known.

In a preferred embodiment the protease to be determined is a serine protease.

A particularly preferred embodiment is one in which the protease to be determined is active in the blood coagulation pathway. Especially preferred in this regard is APC.

Preferably, the body fluid sample is provided as a known amount of blood, or a blood derived product such as serum or plasma.

The immobilized antibody composition in step (a) can be comprised of polyclonal or monoclonal antibodies, with monoclonal antibodies being preferred. When the protease to be determined is APC it is preferred that the immobilized antibody composition be comprised of monoclonal antibody molecules. Representative monoclonal antibody molecules are those described in Example 1 for APC. Particularly preferred is a monoclonal antibody composition that is produced by the hybridoma C3-Mab.

The immobilized antibody composition of step (a) is made serine protease-free by contact with an irreversible serine protease inhibitor in an amount sufficient to inhibit serine protease activity associated with the antibody composition. Particularly preferred irreversible serine protease inhibitors are PMSF, pAPMSF, and DFP.

The first admixture is maintained in step (b) for a time period sufficient for the irreversible inhibitor to come in contact with serine proteases and inactivate them. A representative of a sufficient time period is described in Example 3a, wherein the irreversible inhibitor is contacted with the immobilized antibody preparation for 30 min.

The excess, unbound irreversible inhibitor is removed from the immobilized antibody composition in step (c) by any method which effects its removal. A representative method of removal is to subject the immobilized antibody composition to a series of washes, as described in Example 3a.

The serine protease-free nature of a preferred composition can be evaluated by a variety of methods known to those of skill in the art. For instance, a convenient way of testing for proteases and confirming their removal is provided by Protease Substrate Gel tablets (Bio-Rad Laboratories, Richmond, Calif.). Another way to confirm the low level of background serine protease activity is described in Example 3b.

In step (d), the body fluid sample is treated with a coagulation inhibiting buffer comprising a reversible serine protease inhibitor prior to contact with the immobilized antibody composition. A particularly preferred coagulation inhibiting buffer is described in Example 4a, wherein blood is drawn directly into 0.3M benzamidine, 0.13M trisodium citrate, 0.1M Hepes, pH 6.8, 0.02% sodium azide. The reversible serine protease inhibitor is one that can bind to the serine protease to be detected and be removed in a subsequent step. In the coagulation buffer noted above, the 0.3M benzamidine is the reversible inhibitor. A representative listing of reversible serine protease inhibitors and the serine proteases with which they react is provided below:

| Serine Proteases | Reversible Inhibitors |
| --- | --- |
| APC | benzamidine, aprotinin |
| thrombin | benzamidine |
| plasmin | benzamidine, aprotinin |

A particularly preferred reversible inhibitor for serine proteases is benzamidine.

Preferred are embodiments wherein the amount of protease present in the body fluid sample admixed in step (e) with the immobilized antibody composition is an amount sufficient to form an admixture having an excess of protease molecules relative to the number of antibody combining sites present in the immunoreaction admixture capable of immunoreacting with the protease molecules.

The immunoreaction admixture of step (e) is maintained in step (f) under immunoreaction conditions for a predetermined time period such as about 10 minutes to about 16-20 hours at a temperature of about 4 degrees C. to about 45 degrees C., such time being sufficient for the protease present in the sample to immunoreact with (immunologically bind) a portion of the anti-protease antibody combining sites present in the immobilized antibody composition to form a first solid-phase protease-containing immunoreaction product (immunocomplex).

Immunoreaction assay conditions are those that maintain the biological activity of the immunochemical reagents of this invention and the protease sought to be assayed. Those conditions include a temperature range of about 4° C. to about 45° C., a pH value range of about 5 to about 9 and an ionic strength varying from that of distilled water to that of about one molar sodium chloride. Methods for optimizing such conditions are well known in the art. Representative conditions are provided in Example 5, wherein the admixture is maintained at room temperature for 1–1.5 hr or overnight at 4° C.

The immunoreaction product is prepared in step (g) for activity determination by removing the reversible inhibitor from the first immunoreaction complex to form an inhibitor-free solid-phase immunoreaction product. Preferred methods of removal subject the solid phase to a series of washes to separate the reversible inhibitor from the solid phase and thereafter recovering the solid phase from the wash buffer. A representative method is described in Example 5, wherein the washing cycle is repeated five times.

The protease activity present in the inhibitor-free solid phase immunoreaction product is determined in step (h) and is indicative of the amount of protease in the body sample. A preferred method of determining the activity of the protease is to add a substrate with which the protease reacts and measure the level of conversion of substrate. A preferred determining method measures the amidolytic activity of APC and utilizes a substrate selected from S-2366, S-2238, and Spectrozyme PCa (available from American Diagnostic, Greenwich, Conn.).

The level of conversion of substrate can be measured by any applicable means known to those of skill in the art. For instance, when chromogenic substrates are used in step (h), conversion can be monitored using a spectrometer, as described in Example 5.

Also contemplated are immunological assays capable of detecting substrate conversion without the use of a label. Such methods employ a "detection means", which means are themselves well-known in clinical diagnostic chemistry and constitute a part of this invention only insofar as they are utilized with otherwise novel methods and compositions. Exemplary detection means include methods known as biosensors and include biosensing methods based on detecting changes in the reflectivity of a surface, changes in the absorption of an evanescent wave by optical fibers or changes in the propagation of surface acoustical waves.

Exemplary of the contemplated diagnostic assay described above is the ECA assay described in Example 5.

G. Diagnostic Kits

The present invention also describes a diagnostic system, preferably in kit form, for assaying for the presence of protease in a fluid sample. A diagnostic system includes, in an amount sufficient for at least one assay, a subject protease activity-free immobilized anti-protease antibody as a separately packaged immunochemical reagent. Instructions for use of the packaged reagent are also typically included.

As used herein, the term "package" refers to a solid matrix or material such as glass, plastic, paper, foil and the like capable of holding within fixed limits a protease activity-free anti-protease antibody of the present invention in an immobilized composition. Thus, for example, a package can be a microtiter plate well to which microgram quantities of a contemplated antibody have been operatively affixed, i.e., linked so as to be capable of being immunologically bound by an antigen, and being protease-free. Preferred are anti-APC antibodies, and particularly MabC3 in an immobilized composition.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, a diagnostic system for assaying for the presence of or to quantitate a protease in a sample, such as blood, plasma or serum, comprises a package containing at least one protease-free immobilized anti-protease antibody composition of this invention.

In preferred embodiments, a diagnostic system of the present invention further includes a substrate with which the captured protease will react, and a label or indicating means capable of signaling the formation of hydrolyzed substrate.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems. Particularly preferred are synthetic chromogenic substrates that form detectable chromophores upon specific cleavage by a protease. Such substrates are well known and are available from commercial sources such as Kabi Diagnostics, Uppsala, Sweden, and American Bioproducts Company, Parsippany N.J.

The diagnostic systems can also include, preferably as a separate package, a specific binding agent. A "specific binding agent" is a molecular entity capable of selectively binding a hydrolyzed substrate species of the present invention or a complex containing such a species, but is not itself a substrate or antibody molecule composition of the present invention. Exemplary specific binding agents are hydrolyzed substrate-specific antibodies, second antibody molecules, complement proteins or fragments thereof, *S. aureus* protein A, and the like. Preferably the specific binding agent binds the hydrolyzed species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention are preferably used in an "ECA" format to detect the quantity of protease in a vascular fluid sample such as blood, serum, or plasma. "ECA" refers to an enzyme capture assay that employs 1) an antibody bound to a solid phase to capture the protease complexed with a reversible inhibitor, and 2) substrate to detect and quantify the amount of an serine protease present in a sample as described herein. A description of the ECA technique is found in Example 5.

Thus, in preferred embodiments, an anti-protease antibody of the present invention is affixed to a solid matrix to form a solid support that comprises a package in the subject diagnostic systems.

A reagent is typically affixed to a solid matrix by adsorption from an aqueous medium although other modes of affixation applicable to proteins and polypeptides well known to those skilled in the art, can be used.

The reagent species, labeled specific binding agent or amplifying reagent of a diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems.

EXAMPLES

The following description provides details of the manner in which particular embodiments of the present invention may be made and used. This description, while exemplary of the present invention, is not to be construed as specifically limiting the invention. Variations and equivalents, now known or later developed, which would be within the understanding and technical competence of one skilled in this art are to be considered as falling within the scope of this invention.

1. Preparation of Monoclonal Antibody C3-Mab a. Purification of PC

Human PC was purified from commercial factor IX concentrate (Proplex; Hyland Therapeutics, Glendale, Calif.) as follows. Lyophilized commercial concentrate (18 bottles) was dissolved in 200 ml of sterile deionized water containing 1 mM diisopropylfluorophosphate (DFP) and dialyzed against starting buffer (0.05M sodium phosphate buffer, pH 5.9, 10 mM EDTA, 10 mM benzamidine hydrochloride, 1 mM DFP, and 0.02% sodium azide). The dialyzed material was applied to a DEAE-Sephadex column (2.5×20 cm; Pharmacia, Piscataway, N.J.) equilibrated in starting buffer and washed with 100 ml of starting buffer. PC was eluted with a linear sodium chloride gradient of 300 ml of starting buffer and 300 ml of starting buffer containing 0.4M sodium chloride at a flow rate of 50 ml/hr. Fractions containing PC, as judged by anticoagulant activity (see below) following activation by thrombin as well as positive antigenic activity immunoreactive with sheep anti-PC polyclonal antisera, were pooled and dialyzed against a buffer containing 0.05M MES-Tris, pH 6.0, 10 mM benzamidine hydrochloride, 2.5 mM calcium chloride, and 0.02% sodium azide. After dialysis, the PC pool was applied to a heparin-Sepharose column (2.5×15 cm; Pharmacia, Piscataway, N.J.) and the elution was effected according to the method of Kisiel or J. Clin. Invest. 64:761-769 (1979)], i.e., with a linear gradient of NaCl formed by 150 ml equilibrating buffer (20 mM MES-Tris, 2.5 mM CaCl$_2$, 1 mM benzamidine, pH 6.0) and 150 ml equilibrating buffer containing 1M NaCl. The flow rate was 1 ml/min and 2 ml fractions were collected. The PC fractions were pooled, dialyzed against 0.01M Tris, 0.08M glycine, 0.1 mM EDTA, pH 8.4, and further purified with preparative polyacrylamide gel electrophoresis at 2° C. to form purified PC.

During purification of PC, the presence of anticoagulant activity was assayed in a Kaolin-activated partial thromboplastin time (APTT) assay following activation of PC test samples with thrombin. For example, to a 100 ul sample of PC, 10 ul of thrombin (300 U/ml; Enzyme Research Laboratories, South Bend, Ind.) were added and the mixture was incubated for 90 min. The thrombin was removed by the addition of 100 ul cationic resin (BioRex 70). This sample was then assayed in an activated partial thromboplastin time assay (APTT) as follows. 0.5-3 $\mu$L of APC or buffer (negative control) were mixed with 50 $\mu$L of Protac solution, prepared according to the manufacturer's instructions (1 U/mL, American Diagnostica, Inc., New York) and then incubated in the Electra 700 cuvette for 460 sec at 37° C. Then 100 $\mu$L of APTT reagent (General Diagnostics, Morris Plains, N.J.) and 100 $\mu$L of PC deficient plasma (George King Biomedical, Inc., Overland Park, Kans.) were added simultaneously, and the mixture was incubated for 200 sec prior to recalcification using 100 $\mu$L 25 mM CaCl$_2$. The activated partial thromboplastin time was then measured in seconds. When buffer was used as a control, the clotting time was 50 sec, but a positive sample had a clotting time of over 80 sec, demonstrating the antithrombolin activity of APC.

Protein concentration was determined spectrophotometrically using an extinction coefficient of 1.41 at 280 nm for human PC and by the method of Lowry et al., J. Biol. Chem. 193:265-275 (1951).

b. Immunization Schedule

Murine Mabs to PC were prepared by a modification of the method of Kohler and Milstein [Nature 256:495 (1975)]. In brief, on Day 1, BALB/c mice were injected intraperitoneally with 35 ug of purified PC (see Example 1.a.) mixed with complete Freund's adjuvant. On days 18 and 25 the mice were injected with 35 ug antigen in incomplete Freund's adjuvant. On day 35, three days prior to cell fusion, 35 ug of purified PC was injected intravenously (IV).

c. Hybridoma Production

Spleen cells ($8.6 \times 10^8$) from immunized mice were fused with P3X63-Ag8.653 (available from ATCC as CRL15800) murine myeloma cells ($1.7 \times 10^8$) using 30% (wt/vol) polyethylene glycol-1000. After two days of $4 \times 10^{-7}$ mol/L aminopterin treatment, the cells were seeded into 96-well microtiter plates at $1.5 \times 10^4$ cells per well. Fused cells were cultured in DMEM (Dulbecco's Modified Eagle's Medium) supplemented with 20% newborn calf serum, 10% NCTC (National Cancer Tissue Culture) 109 medium, oxalacetate (1 mmol/L), pyruvate (0.45 mmol/L), glutamine (2 mmol/L), penicillin and streptomycin (5 ml each to 720 medium), Hepes (20 mmol/L), hypoxanthine ($1 \times 10^{-4}$ mol/L), and thymidine ($3 \times 10^{-5}$ mol/L).

d. Initial Screening Protocol

Ten days post fusion, the hybridomas were screened for growth. Approximately 15% were growing. The supernatants from the growing cells were tested on day 19 for reactivity against purified PC by a direct binding radioimmunoassay (RIA). For these assays, each well of a 96-well plastic microtiter plate (Immulon II microtiter plates, Dynatech Laboratories) was coated overnight at 4° C. with 6 ug/ml PC in 0.05M borate buffer, pH 8.4. The plates were washed with 50 mM Tris/HCl, 0.14M NaCl, 0.05% NaN$_3$, pH 7.2, and 7 mM EDTA (TBS/EDTA), and then coated with 3% BSA in TBS/EDTA (blocking buffer) for 1 hr at 37° C. The plates were washed three times with TBS/EDTA. Fifty ul of supernatant from each clone Were added to each well, along with 5 ul of 70 mM EDTA, and incubated for 1 hr at room temperature. The plate was washed four times with Buffer A/BSA+EDTA (50 mM Tris/HCl, 0.14M NaCl, 0.05% NaN₃, 0.1% BSA, 1.5 mM MgCl₂, 0.05% Tween-20, pH 7.2, 7 mM EDTA). Iodinated rabbit anti-mouse IgG (diluted in Buffer A/BSA+EDTA) was added to each plate and it was allowed to incubate 2 hr at 37° C. Finally, the plate was washed four times with Buffer A/BSA+EDTA, the plate was dried, and the wells cut out and counted. Wells demonstrating radioactivity higher than that recorded in control plates (not coated with PC or not treated with antibody) were indicative of immunoreaction of the iodinated second antibody with anti-PC bound to ummobilized PC, and thus were deemed to have been contacted with momoclonal antibody immunoreactive with PC.

Many hybridomas, including hybridomas 22A101CS3B2 (also referred to herein as C3), C1A, C1B, C2, C4, C5, C9, and C10, were determined by these procedures to immunoreact with PC and were then cloned by limiting dilution.

e. Cloning and Production of Ascites

Thymus cells (5×10⁵/ml) from BALB/c mice were added to the wells as a feeder layer during cloning.

The clones were evaluated in the above-described assay for production of antibodies specific for PC. Clones that were again found positive were recloned by the same procedure to ensure monoclonality and were again screened by one of the assays. Positive cell lines were selected for injection (1×10⁶ cells per animal) into the peritoneal cavity of BALB/c mice that had been injected with 300-500 ul pristane about 10 days prior to injection with hybridoma cells.

f. Secondary Screenings i. Use of Antibody to Capture and Immobilize PC

The ascitic fluids obtained from mice injected with clones producing monoclonal antibodies C3, C4, and C10 were screened for their ability to bind radiolabelled PC as follows. The IgG fractions were purified from the fluid using anion exchange chromatography, as described in Geiger et al. (1989), Thromb. Haemost. 61:86-92 and Clezardin et al. (1985), J. Chromatogr. 319:67-77. Briefly, 100 ul mouse ascites fluid in 100 ul of 20 mM carbonate, pH 9.0, was applied to a Mono Q HR 20/20 column on a Pharmacia FPLC apparatus at a flow rate of 1.0 ml/min. Elution was by a step gradient of 0% buffer B (0.05M Tris, 1M NaCl, pH 7.4) for 5 min, 0-20% B in 30 min, and 20-35% B in 10 min.

50 ul of each purified monoclonal anti-PC antibody or nonspecific mouse IgG (62.5 ng - 4 ug per well) in 0.01M Na-carbonate buffer, pH 9.6, were used to coat wells of Falcon 3911 Microtest II plates overnight at 4° C. The plates were washed three times with PBS, pH 7.4, containing 2% BSA, 0.05% Na-azide, 0.05% Tween 20 and three times with PBS, pH 7.4, containing 0.05% Na-azide, 0.05% Tween 20. The remaining binding sites were blocked with 200 ul of 3% BSA in PBS, 1 mM EDTA and 0.05% Na-azide, 0.05% Tween 20, pH 7.4 for at least 1 hr at 37° C. ¹²⁵I-PC was prepared by iodination of purified PC (see Example 1.a.) using the standard chloramine T method [McConahey et al. (1966) Int. Arch. All. Immunol. 29:185–189]. Fifty ul of ¹²⁵I-PC (200,000 CPM/well, specific activity 10 uCi/ug) in 0.01M Na-phosphate buffer containing 0.14M NaCl (PBS), 3.0% BSA, 1 mM EDTA, 0.05% Tween 20, 0.05% Na-azide, pH 7.4, were added to each well and the plate was incubated for 90 min at 37° C. After washing the plates, wells were cut out and counted in a Micromedic 4/600 automatic gamma counter. Wells demonstrating radioactivity higher than that recorded in control please (coated iwth control IgG or not contacted with ¹²⁵I-PC) were indicative of immunoreaction between iodinated PC and anti-PC monoclonal antibody, and thus were deemed positive.

The data indicated that all tested monoclonals immunoreacted with PC antigen. Mouse control IgG did not bind PC. The order of affinity of the monoclonals was C3>C4>C10. As monoclonal C3 had the highest affinity for PC, it was selected for use in the APC assay described below (Example 5).

ii. Antibody Binding to PC (immunoblotting)

For immunoblotting studies, aliquots of reduced and non-reduced purified PC was brought to a constant volume (usually 40 ul) in TBS-1.25% ovalbumin, and electrophoresed on 10% polyacrylamide gels at 10 mA for 16 hours. Details of the immunoblotting procedure were as described in Berrettini et al. Blood 68:455–462 (1986) and Schwarz et al. Thromb. Haemostas, 56:382–386 (1986), except that detection was with ¹²⁵I-secondary antibody at 500,000 cpm/ml.

For quantitative immunoblotting, samples were pipetted into conical Eppendorf tubes containing the carrier protein in 2% BSA in TBS, and then sample buffer was added. Before application to the gel, the mixture was centrifuged (14,000 rpm, Beckman Microfuge B) for 15 sec and applied to the gel using a Hamilton syringe. Antibodies were centrifuged (14,000 rpm) for 15 sec at ambient temperature prior to use and buffers were filtered (Whatman 1 paper filter) to minimize background.

Discontinuous SDS 10% polyacrylamide gel electrophoresis was then performed on the applied samples as described above in 1.5 mm thick slab gels with 4% stacking gels containing 0.5 mM EDTA. After electrophoresis, separated proteins were immediately electrotransferred from the gel to a nitrocellulose (NC) membrane (Trans Blot, BioRad) at 50 V for two hours in a TE-52 Electrophoresis Unit with a circulating cooling system (Hoefer Scientific Instruments, San Francisco, Calif.) containing 50 mM Tris, 45 mM glycine, pH 8.5, 20% (v/v) methanol and 0.02% SDS as transfer buffer. After transfer, the NC membrane was blocked in BLOTTO (bovine lacto transfer technique optimizer) containing 1 uM para-amidinophenyl-methyl-sulfonylfluoride and 0.02% NaN₃ for one hour at room temperature on a rocking platform. BLOTTO is 200 g dry milk in 400 ml water, 1.33 ml antifoam, 40 ul of 100 mM pAPMSF; stirred for 20 min. Then, 400 ml of 10×PBS, pH 7.2 and 0.0001% thimersol are added. The volume is brought to 4 liters with water, stirred and filtered. Subsequently, the NC membrane was exposed to primary antibody (i.e., monoclonal anti-PC diluted 1:3000 in 50 ml BLOTTO) for three hours at room temperature on a shaker with the NC membrane freely floating. The NC membrane was then washed three times with BLOTTO for a total of 30 min and incubated in 50 ml BLOTTO containing ¹²⁵I-labeled secondary antibody (goat anti-PC at 1:400) for one hour. In some experiments immunodetection of PC was achieved by incubating the NC membrane with radiolabeled antigen, $^{125}$I-PC, at 5,000,000 cpm/ml, in place of secondary antibody. After washing three times with BLOTTO and once with phosphate buffered saline, pH 7.4, the NC membrane was air-dried and exposed to Kodak X-OMAT RP film at −70° C. in a cassette equipped with intensifying screens (Du Pont De Nemours Inc., Wilmington, Del.). For quantitation, strips of the NC membrane corresponding to the PC mobility on the X-ray film were cut and the radioactivity bound to the NC membrane measured in a gamma counter (Micromedic System 4/6000).

Eight anti-PC murine monoclonal antibodies were prepared as described in Example 1.F.i. and tested by immunoblotting to 49 ng of nonreduced purified PC and 5 μg of reduced PC (sensitivity to reduced PC was much lower than sensitivity to nonreduced PC thus a greater quantity of reduced PC was used in the immunoblot). Two antibodies (C1A and C1B) were positive for heavy chain, four were positive for light chain (C3, C5, C9 and C10), and two (C2 and C4) were negative. Single chain PC was detected weakly on the reduced blot by C3, C5, and C9, and more strongly by C10.

g. Enrichment of C3-Mab

Murine monoclonal antibodies specific for human PC light chain antibodies were further purified by immunoaffinity.

i. Preparation of PC column

C3-Mab antibodies purified from the Mono Q-HR/5 column (Example I.f.i.) were coupled to CNBr-activated Sepharose 4B (Pharmacia; 3 mg protein/ml gel) in coupling buffer (0.5 mol/L NaCl, 0.05 mol/L borate, pH 8.5) overnight at 4° C. to form C3-sepharose. The affinity column was used to purify PC as follows. Five grams of factor IX concentrate (740 mg prothrombin complex/gr powder, vapor heated; gift from Dr. Hans Peter Schwarz, Immuno, Austria) was passed over C3-Sepharose in 250 ml buffer containing 0.1 mol/L NaCl, 2 mmol/L EDTA, 2 mmol/L benzamidine, 0.02% Na-azide, 0.02% Tween-20, 0.02 mol/L Tris-HCl, pH 7.4, and subsequently eluted with 3 mol/L NaSCN in 1.0 mol/L NaCl, 4 mmol/L benzamidine, 2 mmol/L EDTA, 0.02% Na-azide, 0.05% Tween-20, and 0.05 mol/L Tris, pH 7.0. The passage rate was 15 ml/hr at room temperature. The column was washed with 6.8 bed volumes of buffer and eluted at a flow rate of 15 ml/hr. The PC was >95% pure when analyzed using sodium dodecyl sulfate-polyacrylamide gel electrophoresis (10% gel; SDS-PAGE). Equivalent results were obtained when expired Proplex (Factor IX complex; Hyland Therapeutics, Glendale, Calif.) was used instead of Factor IX.

ii. Contacting C3 to Immunoaffinity Column

The purified IgG fraction from the Mono Q-HR/5 column (Example 1.f.i.) then was further purified by contact with the PC-Sepharose column as follows. Purified IgG was absorbed to immobilized PC in 0.01M Tris, pH 7.4, 0.14M NaCl (TBS), 0.02% Na-azide, and subsequently eluted using either 3M Na-thiocyanate in 0.05M Tris, pH 7.4, 1.0M NaCl, 0.02% Na-azide or 0.1M glycine, pH 2.5, 0.1M NaCl. The thiocyanate eluate was dialyzed against 0.05M Tris, pH 7.4, 0.5M NaCl; the glycine eluate was dialyzed against TBS. Both eluates were stored at −70° C. until use. The two antibody preparation methods gave equivalent results.

2. Preparation of immobilized C3-Mab

The wells of a 96 well flat bottom Immulon II microtiter plate (Dynatech Laboratories, Chantilly, USA) were coated with 250 μl of C3-Mab (50 to 100 μg/ml, purified as described in Example 1.g.ii.) in coating bufferat 4° C. The following coating buffers were used with equivalent results: 0.01M sodium carbonate, pH 9.2, 0.02% Na-azide; or 0.02 sodium carbonate, pH 8.5, 0.02% Na-azide; or 0.02 Tris-HCl, pH 7.8, 0.02% Na-azide. Coating buffer alone was added to negative control plates. The plates were allowed to incubate for 14 hours at 4° C. The plates were then blocked with 1% casein in coating buffer (300 μl/well) for at least 1 hour at 37° C. or overnight at 4° C., the latter being preferred. [The blocking buffer was stored at 4° C. with immobilized soybean trypsin inhibitor (1 ml bead to 500 ml buffer; Pierce, Rockford, Ill.), and was filtered through 0.2 um pore size syringe filter prior to use.] The C3-Mab coated plates were washed with washing buffer (0.02M Tris, pH 7.4, 0.15M NaCl, 0.02M EDTA, 0.02% Tween 20, 0.02% Na-azide; filtered with 0.2 um pore size filter) and stored at 4° C.

3. Preparation and analysis of serine protease-free immobilized C3-Mab a. Preparation

The blocked C3-Mab microtiter plates (prepared in Example 2) were treated with 25 μl/well of either DFP (diisopropylfluorophosphate; 10 μg/ml in 0.14M NaCl; Sigma Chem. Co., St. Louis, Mo.), or pAPMSF [(p-amidinophenyl)methanesulfonyl fluoride; 10 μg/ml, in 0.1M sodium acetate, pH 6.0; Chemicon, El Segundo Calif.] for 30 min. at 4° C. The wells then were washed with dilution buffer (0.05M Hepes, pH 7.24, 0.2M NaCl, 0.05M benzamidine, 0.02M EDTA, 0.4% casein, 0.6% ovalbumin, 2% BSA, 0.04% Na-azide, and 0.05% Tween-80; filtered with 0.2 μm pore size filter) to which soybean trypsin inhibitor had been added prior to benzamidine addition. To each well was added 300 μl washing buffer, and the plates were stored at 4° C. for no longer than one month.

b. Analysis

Parallel experiments were performed to measure substrate hydrolysis in the presence and absence of contaminating serine proteases associated with the immobilized antibody composition. Thus, four different treatments were applied to four sets of 16 wells as follows:

| Steps | Treatments | | | |
|---|---|---|---|---|
|  | 1 | 2 | 3 | 4 |
| coat with C3-Mab | + | + | − | − |
| block with casein | + | + | + | + |
| washing buffer | + | + | + | + |
| pAPMSF | − | + | − | + |
| washing buffer | − | + | − | + |
| S-2366 substrate | + | + | + | + |

In the four treatments noted above, a "+" denotes that the step was performed, a "−" denotes that the step was not performed. The coating with C3-Mab, blocking with casein, and washing buffer were as in Example 2; the addition of pAPMSF was as in Example 3a. The last washing step was repeated five times with washing buffer. The synthetic chromogenic substrate for APC, S-2366 (100 ul; Kabi Diagnostica, Uppsala, Sweden) was prepared according to Example 5, and was added to the appropriate wells, and the plates were sealed and placed in a wet chamber for a week at 37° C. The plates then were read at an absorbance of 405 nm and 630 nm, the higher absorbance necessary for reading higher enzymatic activity.

Statistical analyses of the resultant data indicated that hydrolysis of S-2366 was significantly faster in wells not treated with the pAPMSF irreversible inhibitor (i.e., treatments 1 and 3) than in wells so treated (i.e., treatments 2 and 4). The presence or absence of antibody did not seem to be a significant factor in hydrolysis of the substrate by contaminating serine proteases. Thus, treatment with pAPMSF decreases the background serine proteases associated with the immobilized antibody.

4. Preparation of Samples for Assay a. Plasma standards

Aliquots of diluted normal pooled plasma (NPP) were used as standards in the enzyme capture assay (ECA; see example 5). Normal plasma standards were prepared from the venous blood of nine healthy volunteers. Blood samples of 1.8 ml were drawn directly into a 0.2 ml anticoagulant mixture of 0.3M benzamidine, 0.13M trisodium citrate, 0.1M Hepes, pH 6.8, 0.02% sodium azide. The plasma samples were pooled and dilutions were made in the range of 6.125–150% by combining NPP and dilution buffer (Example 3a) in one of the following two alternative proportions:

|  | Dilution Buffer | | |
|---|---|---|---|
| NPP | Method 1 | Method 2 | Dilution |
| 15 (ul) | 185 (ul) | 285 (ul) | 150% |
| 10 | 190 | 290 | 100% |
| 5 | 195 | 295 | 50% |
| 2.5 | 197.5 | 297.5 | 25% |
| 1.25 | 199 | 199 | 12.5% |
| 0.625 | 200 | 200 | 6.25% |

Aliquots of NPP were stored at −70° C.

b. Experimental Samples

For assays of APC activity in plasma from normal blood donors, venous blood (4.5 ml) from 22 healthy fasting volunteers (14 female, 8 male) were collected into blood collection tubes (Vacutainer, Baxter, USA) by standard venepuncture after informed consent at the General Clinical Research Center at Scripps Clinic, La Jolla, Calif. The blood was transferred into a polyethylene centrifuge tube holding 0.5 ml of 0.3M benzamidine, 0.14M Na-citrate to yield a final concentration of 0.03M benzamidine. The plasma then was prepared by centrifugation (3000xg, 3 min, 4 C.; within 60 minutes of blood drawing), frozen, and stored at −70°.

c. Purified APC Standards

Purified APC was used as standard in the ECA (Example 5). APC was prepared by isolating PC according to Example 1.a. and then activating it. Activation was by the method of Marlar et al. (1982), Blood 59:1067. Briefly, PC in tris-buffered saline (0.15 mol/L NaCl, 0.01 mol/L Tris, pH 7.4; TBS) was activated using thrombin-Sepharose beads. Four mg thrombin (2880 U/mg; Enzyme Research Laboratories, South Bend, Ind.) were coupled to 2 ml CNBr$_a$-Sepharose 4B in coupling buffer (0.5 mol/L NaCl, 0.05 mol/L borate, pH 8.5) overnight at 4 C. The gel was washed with a washing buffer (TBS), the TBS was removed by centrifugation (1000 rpm, 1 min) and TBS containing purified PC was added. The PC was activated during end-to-end rotation of the immobilized thrombin-PC solution mixture at room temperature. The activation of the PC zymogen was monitored using chromogenic peptide substrate S-2366 (Kabi Diagnostica, Uppsala, Sweden), and reading absorbance at 405 nm and/or 630 nm for higher enzymatic activity. The activation was stopped by removing the thrombin-Sepharose beads (centrifugation, as above) when no further increase in amidolytic activity was observed.

The APC was tested for anticoagulant activity as described in Example 1.a. APC preparations exhibiting maximal specific activity (250 U/mg) were used as standards in the APC ECA (Example 5).

Standard serial dilutions of purified human APC in the range of 38 ng/l to 10 mg/l were made in dilution buffer, aliquots were frozen in liquid nitrogen and stored at −70° C.

5. Enzyme Capture Assay (ECA)

Prior to assay, APC standards and plasma samples were further diluted in a dilution microplate using one part sample and either 20 (Method 1, Example 4a) or 30 parts (Method 2, Example 4.a.) dilution buffer to reach a total volume of 210 or 310 μl respectively. Each plate had at least one series of purified APC standards in addition to the unknown samples and NPP standards.

To capture APC and PC antigen, aliquots (50–200 μl) from the diluted APC standards, plasma controls and experimental samples (Example 4) were transferred to C3-Mab coated microtiter plates (Example 2) containing an appropriate volume of dilution buffer to yield a final quantity of fluid equal to the volume of buffer used to coat the plate with antibody. The plates were incubated at room temperature for 1–1.5 hours or overnight at 4° C. with equivalent results. Following the adsorption step, washing buffer (250 ul) was added to remove the unbound proteins and benzamidine. The covered plates were vigorously shaken on a rocking table (2–5 minutes, 200–260 rpm) and then the washing buffer was removed by rapping the inverted plates on layers of clean paper towels for thorough removal of residual liquid. The washing cycle was repeated for at least five times within 30 min for most complete removal of the benzamidine and especially for removal of contaminating plasma enzymes that could nonspecifically bind to the plate.

Following the last washing cycle, a synthetic oligopeptide chromogenic substrate for APC, S-2366 (0.45–1.0 mM in TBS, pH 8.0, 0.05% Na-azide) was added to the wells. S-2366 is <Glu-Pro-Arg-pNA (Kabi Diagnostica, Uppsala, Sweden), it was prepared aseptically at 4° C. and filtered through a 0.2 μm filter. The lyophilized substrate was diluted to 4 mM using sterile water. Prior to the assay the substrate was further diluted to 0.4 mM using filtered washing buffer in a disposable sterile reagent tray. Hydrolysis of the substrate was monitored at 405 nm (or at 405/630 nm) over time and recorded using Bio-Tek Microplate Autoreaders EL 309 or EL 312 (Bio-Tek Instruments, Inc., Highland Park, Winooski, Vt.). In some experiments, substrates other than S-2366 for APC were used with satisfactory results, e.g., S-2238 (Kabi Vitrum, Uppsala, Sweden), and Spectrozyme PCa (American Diagnostica, Greenwich, Conn.). When the standard APC concentration range covered more than 3 orders of magnitude, the plates were read repeatedly over various appropriate periods of time. In between readings, the plates were sealed and stored in wet chambers to avoid evaporation of liquid from the wells. Normal plasma levels of APC were measured by developing the plates at 4° C. in most experiments.

Special care was taken to avoid microbial and enzyme contamination of the samples, buffers, microplates and substrate. Sterile water, plasticware, gloves and mask were used since microbial and other contaminating enzymes hydrolyze chromogenic substrates resulting in background activity. The enzyme assay step could be repeated by removing the hydrolyzed substrate and introducing fresh S-2366 solution into the wells. The bound APC retained its amidolytic activity for weeks at 4° C.

a. Specificity and Sensitivity of ECA for APC

Diluted purified APC samples were evaluated in the ECA as described in Example 5. Standard curves were generated for the amidolytic activity of APC samples in various concentration ranges and analyzed at various times of incubation (20 min, 60 min, 12 days). The 12 day incubation was employed to measure statistically significant changes in absorbance at very low APC concentrations ($10^{-2}$ to $10^{-4}$ $\mu g/\mu l$) compared to control wells in which no APC was added.

Figure 1B:
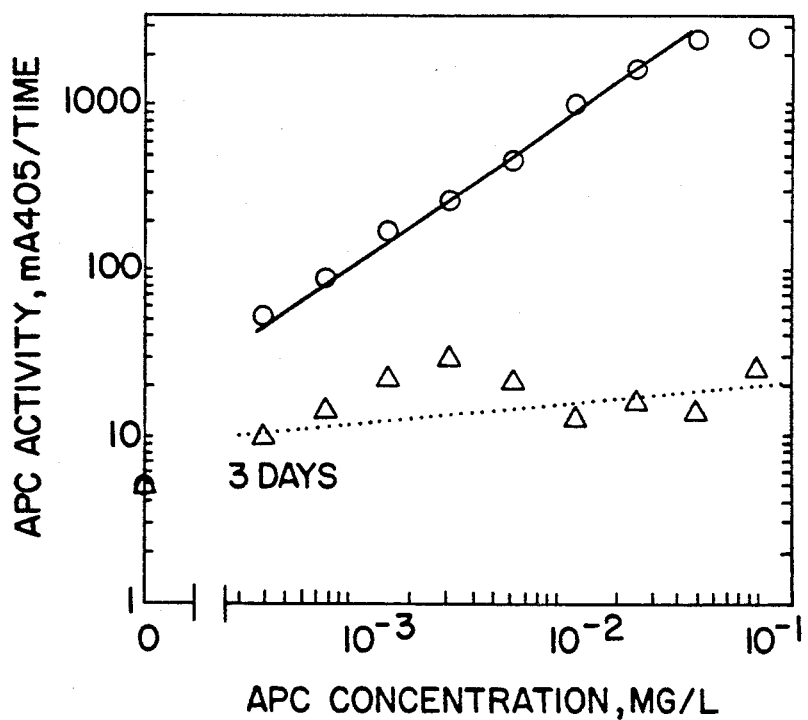

The data from these analyses are shown in FIG. 1. Panel A shows the results produced using the standard curves generated over a wide concentration range and various times of incubation. Hydrolysis of the chromogenic substrate was linear with the concentration of APC at each assay time ($r > 0.95$, $P < 0.01$ for each displayed standard). Thus, the ECA for APC is sensitive down to 0.7 pM APC and linear standard curves covering 0.7 pM to 0.1 $\mu$M APC can be generated.

Panel B provides the data generated when the APC standards were treated with anti-PC antibodies prior to the ECA (triangles), and compares it to that generated with PC not treated with antibody (open circles). Preincubation was accomplished by incubating immunoaffinity purified polyclonal anti-PC antibodies ($\alpha$PC-Pab; 381 ug/ml final concentration) in the detection plate for at least 20 min at room temperature. Incubation times with substrate were for three days after the preincubation. The polyclonal antisera was prepared in sheep using purified PC as immunogen and following well known standard polyclonal antisera production protocols.

Hydrolysis of S-2366 was inhibited by more than 95% (triangles in FIG. 1B) when APC in a concentration range of $3.8 \times 10^{-5}$ to 5 mg/l was preincubated with $\alpha$PC-Pab ($P < 0.01$ for all measurements). This provided evidence that the measured amidolytic activity was caused by APC.

b. Specificity and Sensitivity of ECA for normal pooled plasma

Figure 2A:
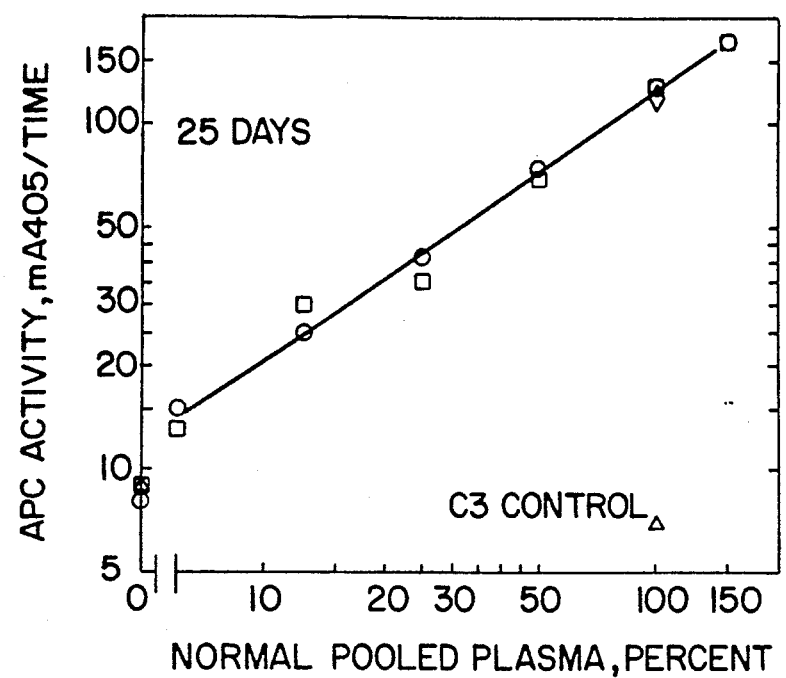
FIGS. 2A and 2B illustrate the APC activity measured in dilutions of pooled plasma samples and correlates the values with APC standard, as described in Example 5b.

To determine if APC was detectable in normal plasma, dilutions of NPP were assayed in the ECA (FIG. 2A). The observed amidolytic activity was linear down to 6% of NPP, with a correlation coefficient of 0.998 ($P < 10^{-5}$).

Figure 2B:
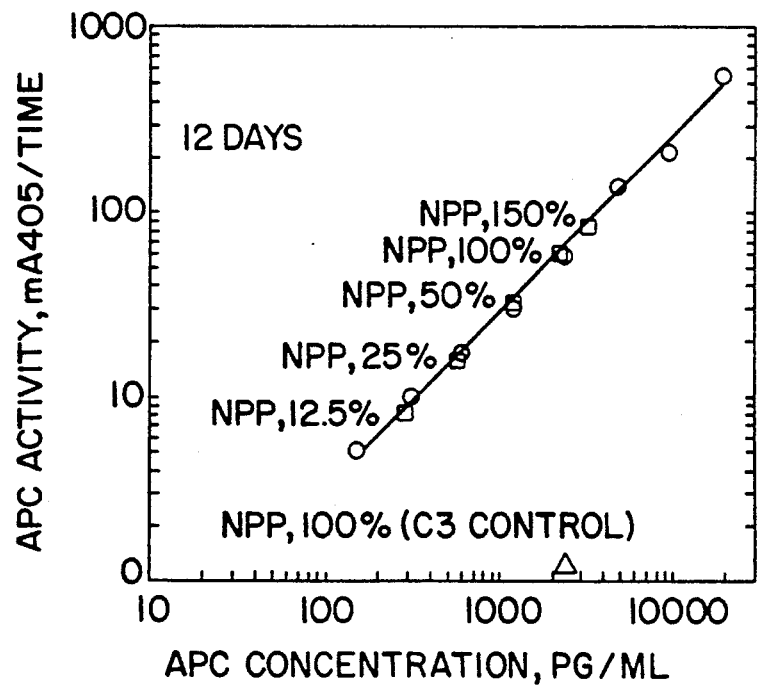

To quantitate APC in NPP, a careful comparison of APC activity in NPP dilutions to that in APC standard curves was made after 12 days incubation. FIG. 2B shows that the amidolytic activity of 12.5%, 25%, 50%, 100% and 150% NPP dilutions corresponded to the amidolytic activity of $0.298 \pm 0.052$, $0.598 \pm 0.096$, $1.186 \pm 0.13$, $2.265 \pm 0.080$ and $3.162 \pm 0.215$ ng/ml of purified plasma-derived human APC standards, respectively ($N = 6$ for each, $r = 0.977$, $P < 10^{-6}$). Thus, APC amidolytic activity of 100% normal pooled plasma was equivalent to the amidolytic activity of 2.27 ng/ml (38 pM) C3-Mab captured purified APC.

The microtiter plate wells that were not coated with the capturing C3 antibody did not exhibit significant amidolytic activity from 100% NPP (triangles in FIG. 2B). The interassay variation of the ECA was 6.4%. The assay was sensitive to 0.3 ng/ml APC in NPP. Since NPP contains 4.3 $\mu$g/ml PC zymogen (70 nM), the APC ECA was sensitive for enzyme concentrations as low as 1:20,000 of plasma PC zymogen levels.

c. APC activity in Experimental Patient Samples

Figure 3:
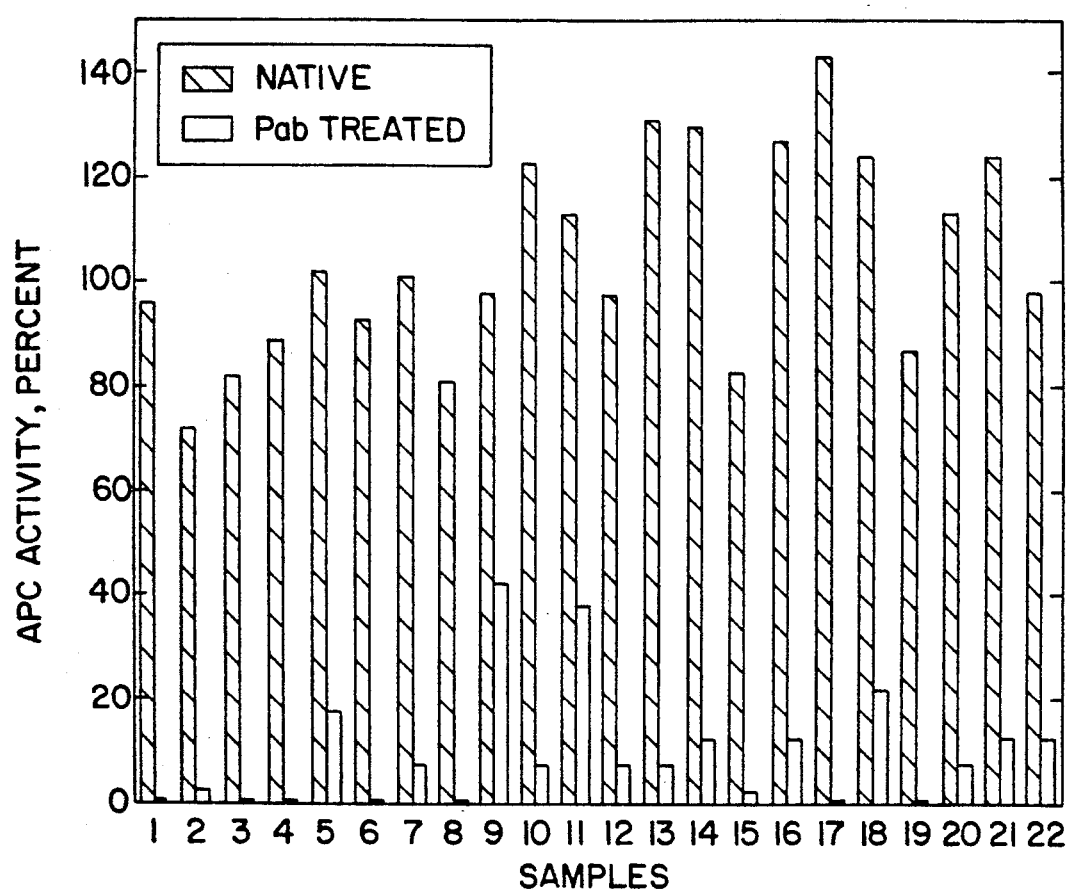
FIG. 3 graphs the APC activity measured in plasma samples from 22 healthy blood donors as measured by the ECA (see Example 5c). The stippled bars represent the APC activity, as percent of the APC standard, for each sample. The open bars show the APC activity for samples pretreated with anti-PC antisera.

The ECA was used to measure the range and variability of APC activity in plasma samples prepared from the venous blood of 22 healthy blood donors. The plasma levels of APC are shown in FIG. 3 as percentages of standard, which was measured alongside serum samples in the ECA.

The amidolytic activity averaged $27.3 \pm 3.2$ mOD/10 days compared to a background of $6.9 \pm 1.3$ for no plasma, and $7.3 \pm 0.8$ for wells that were not precoated with the capturing C3-Mab before incubation with plasma samples. The APC levels ranged from 72% to 143% of the Npp standard. averaging $104.9 \pm 19.6\%$.

Pretreatment of the plasma samples with $\alpha$PC-Pab resulted in a significant decrease in the observed APC amidolytic activity in the ECA, similar to the inhibition observed for incubation of purified APC standards with $\alpha$PC-Pab ($\alpha$PC-Pab controls; see Example 6). The observed amidolytic activity for 20 out of the 22 samples following this treatment was within mean background+2SD, suggesting that APC activity was almost completely blocked or removed by $\alpha$PC antibodies. Single antibody treatment of samples 9 and 11 did not reduce the observed enzyme activity to background level (FIG. 3). However, repeated antibody treatment of these samples reduced APC activity to background activity levels in both samples. These results demonstrate the presence of APC in the plasma of 22 normal subjects.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A method for determining the amount of a protease in a body fluid sample comprising the steps of:
   a) contacting an immobilized antibody molecule composition, comprising antibody molecules affixed to a solid support, with an irreversible protease inhibitor in an amount of inhibitor sufficient to inhibit any protease associated with the composition to form a first admixture, said antibody molecules immunoreactive with said protease to form an immunoreaction complex having protease activity and the ability to bind a reversible protease inhibitor;
   b) maintaining the first admixture for a time period sufficient for said irreversible protease inhibitor to inhibit said protease and form a protease activity-free immobilized antibody composition;

c) removing excess irreversible protease inhibitor from said protease activity-free immobilized antibody composition formed in step (b);

d) admixing a body fluid sample with a coagulation inhibiting buffer containing a protease inhibiting amount of said reversible protease inhibitor, to form a second admixture;

e) admixing said second admixture with the protease activity-free antibody composition formed in step (c) to form an immunoreaction admixture having a liquid phase and a solid phase;

f) maintaining said immunoreaction admixture under immunoreaction conditions for a time period sufficient for said protease present in said body sample to immunoreact with the antibody molecules present on the solid support and form a first solid-phase immunoreaction product;

g) removing the reversible protease inhibitor from said first solid phase immunoreaction product to form an inhibitor-free solid-phase immunoreaction product; and h) determining the amount of said protease present in the inhibitor-free solid-phase immunoreaction product formed in step (g) and thereby the amount of protease in the body sample.

2. The method of claim 1, wherein said protease is a serine protease.

3. The method of claim 2, wherein the serine protease is activated protein C (APC).

4. The method of claim 3, wherein the immobilized antibody molecule composition of step (a) comprises C3 monoclonal antibody molecules.

5. The method of claim 2, wherein the irreversible protease inhibitor of step (a) is selected from the group consisting of PMSF, paPMSF and DFP.

6. The method of claim 2, wherein the reversible protease inhibitor of step (d) is selected from the group of benzamidine and aprotinin.

7. A method of claim 1, wherein said determining in step (h) comprises the steps of:

(i) admixing the inhibitor-free solid-phase immunoreaction product formed in step (g) with a protease substrate to form a substrate reaction admixture;

(ii) maintaining the substrate reaction admixture under substrate reaction conditions for a time period sufficient for the protease in the solid phase to catalyze the substrate and form a substrate reaction product; and (iii) determine the amount of substrate reaction product formed and thereby the amount of immunoreaction product formed in step (g).

8. The method of claim 7 wherein said protease substrate is a synthetic chromogenic substrate.

9. The method of claim 1, wherein said removing in step (g) comprises the steps of:

subjecting said first solid phase immunoreaction product to a series of washes for separating the reversible protease inhibitor from the solid phase, and recovering the washed solid phase to form the inhibitor-free solid-phase immunoreaction product.

* * * * *